United States Patent [19]

Perricone

[11] Patent Number: 5,965,618

[45] Date of Patent: Oct. 12, 1999

[54] TREATMENT OF SCAR TISSUE USING LIPOIC ACID

[76] Inventor: Nicholas V. Perricone, 27 Coginchaug Ct., Guilford, Conn. 06437

[21] Appl. No.: 08/971,820

[22] Filed: Nov. 17, 1997

[51] Int. Cl.⁶ .......................... A61K 31/20; A61K 31/385

[52] U.S. Cl. ............................................ 514/558; 514/440

[58] Field of Search ...................... 514/558, 440

[56] References Cited

U.S. PATENT DOCUMENTS

| | | | |
|---|---|---|---|
| 5,084,481 | 1/1992 | Ulrich et al. .............................. | 514/557 |
| 5,472,698 | 12/1995 | Rawlings et al. ......................... | 424/401 |
| 5,569,670 | 10/1996 | Weisher et al. .......................... | 514/440 |
| 5,693,664 | 12/1997 | Wessel et al. ............................ | 514/440 |
| 5,728,735 | 3/1998 | Ulrich et al. .............................. | 514/560 |

OTHER PUBLICATIONS

Yu et al. 126;CA 1354475.

Primary Examiner—Russell Travers
Attorney, Agent, or Firm—St. Onge Steward Johnston & Reens LLC

[57] ABSTRACT

Scar tissue is reduced or inhibited by application of a composition containing lipoic acid and/or a lipoic acid derivative such as dihydrolipoic acid, a lipoic or dihydrolipoic acid ester, a lipoic or dihydrolipoic acid amide, a lipoic or dihydrolipoic acid salt, and mixtures of any of these. Some compositions further comprise α-hydroxy acids or acid derivatives such as glycolic and/or lactic acid, fatty acid esters of ascorbic acid such as ascorbyl palmitate, and/or tocotrienol. In some embodiments, a silicone gel sheet with added lipoic acid and/or a lipoic acid derivative and optional other ingredients is topically applied to scar tissue to diminish them.

34 Claims, No Drawings

TREATMENT OF SCAR TISSUE USING LIPOIC ACID

TECHNICAL FIELD

This invention relates primarily to methods and compositions for the treatment of scar tissue, particularly hypertrophic and keloid scars and straie distensae (stretch marks). Scars typically result from repair of damaged tissue, and this damage may be following trauma, burns, or disease. Because scars are cosmetically distracting and sometimes symptomatic, producing bothersome itching, burning, stinging or painful sensations, there is considerable interest in their treatment.

BACKGROUND OF THE INVENTION

Scars result from wound healing, which occurs in three separate phases: inflammation, formation of granulation tissue, and matrix formation. (For a review, see Sahl, W. J., and Clever, H., *Internat. J. Derm.*, 1994, 33: 681–691 (part I) and 763–769 (part II)). During the first phase, damage to endothelial cells, complement, and platelets at the wound site release chemotactic factors that result in the infusion of neutrophils, lymphocytes and macrophages, which aids in the removal of infection and foreign debris. As in all inflammatory processes, there is generation of free radicals, which damages cell membranes and results in formation of oxidized proteins and fats, and cross-linked new collagen, laying a scaffold for the next phase.

At the end of the inflammatory phase, the granulation phase begins with an influx of fibroblasts and endothelial cells to the wound. Other key cells in this phase are macrophages and platelets. Macrophages induce the beginning of granulation by releasing platelet-derived growth factor (PDGF), tumor necrosis growth factor (TGF)-α, and an epidermal growth factor-like substance. Activated platelets release epidermal growth factor (EGF), PDGF, TGF-α, and TGF-β. Together these play roles in the re-epithelialization process wherein keratinocytes cells migrate in sheaths over a provisional matrix consisting primarily of fibrin, fibronectin, type V collagen, and tenascin, and produce their own fibronectin receptors.

Once re-epithelilization has occurred, keratinocytes resume their normal differentiated form, and matrix formation begins. Matrix formation consists primarily of the construction of derma matrix, which is regulated by fibroblasts. Chemotaxis of fibroblasts results in the production of abundant quantities of hyaluronate, fibronectin, and types I and III collagen. These components comprise the bulk of the provisional extracellular matrix in the early part of this wound repair phase. Hyaluronic acid (HA) creates an open-weave pattern in the collagen/fibronectin scaffold, facilitating fibroblast movement. HA production falls after about the fifth day of wound healing, and levels of chronroitin sulfate in dermatan sulfate increase. Fibronectin deposits in the collagen, and wound contraction begins. Biochemically during the contraction stage, hyaluronidase and proteinase are present, type I collagen synthesis is stimulated, and increased levels of chronroitin sulfate, dermatin sulfate and proteoglycans are observed; together these restructure the matrix. At the end of the healing process, the final scar shows collagen fibers mostly parallel to the epidermis.

Hypertrophic and keloid-type scars result in extension of scar tissue so that a bulky lesion results. A keloid is an exuberant scar that proliferates beyond the original wound. It should be noted that keloids only occur in humans, often causing burning, stinging and itching sensations as well as cosmetic embarrassment. The etiology of unsightly keloid formation is not known. However, in keloids, fibronectin formation continues for years, while fibronectin formation in normal scars disappears within a few days after wound closure. Keloid scars exhibit a high rate of collage synthesis in comparison to normal scars, and a low proportion of cross-linked collagen.

Hypertrophic scars sometimes are difficult to distinguish from keloid scars histologically and biochemically, but unlike keloids, hypertropic scars remain confined to the injury site and often mature and flatten out over time. Both types secrete larger amounts of collagen than normal scars, but typically the hypertrophic type exhibits declining collagen synthesis after about six months. However, hypertrophic scars contain nearly twice as much glycosaminoglycan as normal scars, and this and enhanced synthetic and enzymatic activity result in significant alterations in the matrix which affects the mechanical properties of the scars, including decreased extensibility that makes them feel firm.

Atrophic scars are characterized by a thinning and diminished elasticity of the skin due to a loss of normal skin architecture. An example of an atrophic scar is striae distensae, also known as stretch marks. Striae commonly occur in postpartum women after childbirth and also during times of larger-than-average weight gain and also in association with steroids. Atrophic scars are sometimes also observed after trauma, infection and disease, and may show loss of surface markings and smoothness or dry, fine wrinkles over time.

Formation of scars, especially hypertrophoic and keloid scars, is dependent on systemic growth factors such as interleukins and other cytokines, and their influence on fibronectin and collagen biosynthesis. Cytokines are released and are present in the wound healing process and sometimes are released in the inflammatory stage. Growth factors and other cytokines vary in the inflammatory stage and are released based, among other complex interactions, upon the redox state of the cells. The presence of free radicals in the inflammatory stage plays an important factor in wound healing. Factors that increase the presence of free radicals, such as infection, radiation, and continued trauma, may instigate hypertrophic and keloid scar formation. It is important to note that cytokines have been suggested to regulate nitric oxide synthetase, which controls the formation of nitric oxide, which plays an important role in signal transduction in the cells. It has also been suggested that nitric oxide synthetase activity is aberrant in keloid scars when compared to normal scar tissue (Lim, T. C., et al., Plastic and Reconst. Surgery, 1996, 98:911–912). Hypertrophic and keloid scars also show inflammatory activity that is not seen in mature scars.

Many scar treatments have been suggested, but few are satisfactory. Treatment of keloid or hypertrophic scars have consisted of surgical excision followed in many cases by graft application. Pressure has also been used to cause scar thinning after injury or scarring. For example, pressure bandages placed over scars have resulted in some scar thinning, but a pressure of at least about 25 mm Hg must be maintained constantly for approximately six months in usual situations for any visually observable effect. Ionizing radiation therapy has also been employed. Other treatments include application of silicone pads to the scar tissue surface, sometimes under pressure provided by an elastomeric bandage, application of silicone gel sheets, with or without added vitamin E (Palmieri, B., et al., *J. Derm.*, 1995, 34: 506–509), and topical or intralesional treatment with corticosteroids.

Scars are one of the strongest forces driving the cosmetic industry. It would be desirable to have alternative, preferably new and improved, treatments for scar reduction and remodeling.

SUMMARY OF THE INVENTION

It is an objective of this invention to provide compositions and methods for the treatment and inhibition of scar tissue, including hypertrophic, keloid, and atrophic scars.

It is another and more specific objective of the invention to provide topical compositions and methods for scar reduction and inhibition based upon topical application of compositions containing lipoic acid and/or lipoic acid derivatives, typically in association with a dermatologically acceptable carrier or vehicle and/or a silicone gel sheet, to scars and to injured skin sites susceptible to scarring.

These and other objectives are accomplished by the present invention, which provides compositions and methods for the treatment and/or inhibition of cutaneous scars, which comprises topical application to the scars or injured skin areas of an effective amount of lipoic acid, lipoic acid derivatives or mixtures thereof. Some embodiments employ compositions containing lipoic acid and/or a lipoic acid derivative in a dermatologically acceptable carrier which is applied to diminish or inhibit scar tissue. Others utilize a silicone gel sheet having added lipoic acid and/or a lipoic acid derivative which is applied to scar tissue.

Ascorbic acid, particularly fat-soluble fatty acid esters of ascorbic acid such as ascorbyl palmitate, can, optionally, also be utilized for further enhancing the efficacy of the therapeutic or prophylactic treatment. In other embodiments, tocotrienols or derivatives thereof or vitamin E compositions enriched with tocotrienols or tocotrienol derivatives such as tocotrienol-enriched fractions of natural oils are included in the lipoic acid composition with or without an ascorbic acid ingredient. Still other embodiments include α-hydroxy acids or their derivatives and the like in the lipoic acid composition with or without other optional ingredients.

In a preferred practice of the invention, the lipoic acid (or derivative) is applied in admixture with a dermatologically acceptable carrier or vehicle (e.g., as a lotion, cream, ointment, soap, or the like) so as to facilitate topical application and, in some cases, provide additional therapeutic effects as might be brought about, e.g., by moisturizing of the affected skin areas. As noted, other ingredients, particularly ascorbyl palmitate and/or tocotrienol and/or an α-hydroxy acid, can be advantageously included in the compositions. In one preferred embodiment, a silicone gel sheet having added lipoic acid and/or dihydrolipoic acid and/or other optional ingredients is applied to scar tissue or injured cutaneous sites susceptible to scarring.

The amount of lipoic acid or derivative thereof (hereinafter referred to collectively as lipoic acid or LA for ease of reference) necessary to bring about enhanced reduction and/or inhibition of scar tissue is not fixed per se, and necessarily is dependent upon the identity and form of lipoic acid employed, the amount and type of any additional ingredients (such as ascorbyl esters, tocotrienol, and/or α-hydroxy acids) used, the user's skin type, and the severity and extent of the patient's scarring. In some typical embodiments, the composition contains from about 0.1% to about 7 weight %, lipoic acid or dihydrolipoic acid. In one embodiment, about 2% to 3% lipoic acid is employed.

DETAILED DESCRIPTION OF THE INVENTION

This invention is based upon the finding that lipoic acid and/or its derivatives are useful for the reduction and inhibition of epidermal and subepidermal cutaneous scar tissue, including underlying membrane and connective tissue typically damaged in various types of skin trauma.

As used herein, the term "lipoic acid" encompasses thioctic acid (1,2-dithiolane-3-pentanoic acid; 1,2-dithiolane-3-valeric acid), $C_8H_{14}O_2S_2$, formula weight 206.32. Lipoic acid was originally identified as a bacterial growth factor present in the water-soluble fraction of liver and yeast. It was found to be necessary for the oxidative decarboxylation of pyruvic acid by *Streptococcus fecalis* and for the growth of *Tetrahymena gelii*, and replaced acetate for the growth of *Lactobacillus casei*. It has been variously known as acetate replacing factor, protogen A, and pyruvate oxidation factor.

Subsequent research showed that lipoic acid (LA) was a growth factor for many bacteria and protozoa, and it served as a prosthetic group, coenzyme, or substrate in plants, microorganisms, and animal tissues. Elucidation of its structure and function determined that it is a co-factor for α-keto-dehydrogenase complexes, typically bound as lipoamide, that participates in acyl transfer reactions. Its reduced form, dihydrolipoic acid, is a potent sulfhydryl reductant. In aqueous systems, both exhibit antioxidant actions. Some experiments have shown that lipoic acid may maintain microsomal protein thiols, protect against hemolysis, and protect against neurological disorders (mentioned in the introduction of Maitra, et al., *Free Rad. Biol. Med.* 1995, 18:823–829). The protective effect of dietary supplementation of LA against ischemia/reperfusion injury in the Langendorff isolated heart model has also been suggested (ibid.). LA has been used in treating liver cirrhosis, atheroschlerosis, and polyneuritis of diabetes mellitus (ibid.). Results of ex vivo rat experiments using butathione sulfoximine suggested LA might be useful in preventing cataracts (ibid.), and the compound was disclosed as an ingredient with others for tyrosinase inhibition in a cosmetic composition for skin whitening (Abstract, Jap. Ap. Pub. 63008315). It has also been used as an antidote to poisonous mushrooms (particularly Amanita species, Merck Index, 11th ed., 1989, entry 9255).

Lipoic acid derivatives include thioctic acid esters, particularly alkyl esters such as fatty acid esters, amides, particularly those isolated from or mimicking naturally occurring lipoamides, salts, particularly alkali metal salts, anhydrides and specifically includes the reduced form, dihydrolipoic acid and its esters, amides and salts. Since lipoic acid is both fat- and water-soluble, it is an advantage of the invention that it can be used in either lipid- or aqueous-based compositions, and it readily crosses cellular membranes and disperses in extracellular and intracellular tissue components. Derivatives may also include those involving other reactive groups known to those skilled in the art. As used herein, the term "derivatives" includes metabolic precursors of lipoic acid. Where lipoic acid derivatives are employed, they must be functionally equivalent to lipoic acid.

As mentioned above, lipoic acid is fat-soluble. Therefore, lipoic acid preparations can be applied neat to scar tissue. It is an advantage of the invention that the active compound is fatty so that it physically contributes to the lubrication of affected skin areas to which it is applied.

However, only effective amounts of lipoic acid are needed to reduce or inhibit scar tissue, so generally topical application to exposed or affected skin sites is accomplished in association with a carrier, and particularly one in which the active ingredient is soluble per se or is effectively solubilized (e.g., as an emulsion or microemulsion) or available when applied in a silicone gel sheet or other linament. Where employed, the carrier is inert in the sense of not bringing about a deactivation of the lipoic acid or derivative, and in the sense of not bringing about any adverse effect on the skin areas to which it is applied.

Suitable carriers include water, alcohols, oils and the like, chosen for their ability to dissolve or disperse lipoic acid and any other ingredients used in the treatment. Generally, even low concentrations of active ingredients in a carrier are suitable, depending upon the application regimen and adjunct ingredients employed. Many embodiments contain from about 0.1% to about 7% by weight LA or LA derivative. Many embodiments contain more than 1 weight % lipoic acid and/or lipoic acid derivative, e.g., from about 1.1% to about 3 to 5 weight % LA. One efficacious embodiment contains from about 2% to about 3% by weight. Examples are illustrated hereafter.

While the carrier for lipoic acid can consist of a relatively simple solvent or dispersant, it is generally preferred that the carrier comprise a composition more conducive to topical application, and particularly one which will form a film or layer on the skin to which it is applied so as to localize the application and provide some resistance to perspiration and/or one which aids in percutaneous delivery and penetration of the active ingredients into lipid layers of the scarred area. Many such compositions are known in the art, and can take the form of lotions, creams, gels or even solid compositions (e.g., stick-form preparations). Typical compositions include lotions containing water and/or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. Such compositions are referred to herein as dermatologically acceptable carriers. Most preferred for skin are those carriers which are fat-soluble, i.e., those which can effectively penetrate skin layers and deliver LA to all skin layers.

Alternative embodiments employ a silicone gel sheet or other linament to which LA and/or an LA derivative has been added. These may be pressure or adhesive bandages. Silicone gel sheets useful in the practice of the invention are typically cross-linked polydimethylsiloxane containing or impregnated with LA and/or an LA derivative. It is an advantage of the invention that LA augments the effectiveness of previously disclosed methods of using silicone pads or gel sheets for diminishing scars (see Palmieri, et al., cited above).

As summarized above, many preferred embodiments of this invention contain at least one other ingredient in addition to lipoic acid. For example, fat-soluble fatty acid esters of ascorbic acid (vitamin C) may be added to the lipoic acid composition in some embodiments. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate.

α-Hydroxy acids and/or their derivatives may also be added to lipoic acid compositions of the invention with or without added ascorbyl esters. As used herein, the terminology "α-hydroxy acid" has reference to and encompasses the general class of organic compounds containing at least one hydroxy group and at least one carboxyl group, and wherein at least one hydroxyl group is located on the α-carbon atom. Typically, the compounds are organic acids having at least one carboxylic acid group and at least one hydroxyl group on the α-carbon atom, and may contain other functional groups including additional hydroxyl and carboxylic acid moieties. Most typically, α-hydroxy acids will have a basic structure of lower aliphatic compounds having from two to six carbon atoms.

The "derivatives" of these α-hydroxy acids most typically will involve derivatives related to the carboxyl functionality, i.e., wherein the hydrogen or hydroxyl portion of the carboxyl moiety is substituted by metallic ions (to form salts), alkoxy groupings (to form esters), ammonium ions (to form ammonium salts), as well as other substitution reactions and products leading to formation of corresponding lactones, anhydrides or amines. However, the derivatives may also include reactions involving the α-hydroxyl group, most notably ketone formation, to form corresponding α-keto carboxylic acids.

Among the hydroxy acids and derivative compounds useful in the present invention are hydroxy monocarboxylic acids such as glycolic acid, hydroxymethylglycolic acid, lactic acid, glucuronic acid, galacturonic acid, gluconic acid, glucoheptonic acid, α-hydroxybutyric acid, α-hydroxyisobutyric acid, α-hydroxyvaleric acid, α-hydroxyisovaleric acid, α-hydroxycaproic acid, and α-isocaproic acid. Also included are di- and tri-carboxylic hydroxy acids such as tartronic acid, tartaric acid, malic acid, hydroxyglutaric acid, hydroxyadipic acid, hydroxypimelic acid, muric acid, citric acid, isocitric acid, saccharic acid, dihydroxymaleic acid, dihydroxytartaric acid, and dihydroxyfumaric acid. Derivatives involving keto groups include keto acids and keto esters such as pyruvic acid, methyl pyrivate, ethyl pyruvate, isopropyl pyruvate, benzoylformic acid, methyl benzoylformate, and ethyl benzoylformate. In some preferred embodiments, α-hydroxy acids having an aliphatic backbone of 2 to 3 carbons such as glycolic and/or lactic acid or their derivatives are employed.

Tocotrienol may also be added to lipoic acid compositions of the invention, alone or in combination with an ascorbyl esters and/or α-hydroxy acids or their derivatives in some embodiments. The term "tocotrienol" encompasses natural and/or synthetic counterparts of tocopherol (vitamin E) that bear unsaturated tails, and include, but not limited to, α-, β-, γ-, and δ-tocotrienols, tocotrienol P25, desmethyl-tocotrienol, didesmethyl-tocotrienol, their synthetic counterparts, their counterparts having methylated or demethylated chroman rings, and mixtures thereof. The double bonds may be cis or trans or mixtures thereof.

Tocotrienol useful in compositions of the invention may be tocotrienol-enriched vitamin E preparations obtained from natural or synthetic sources, such as those obtained by removal of tocopherol from vitamin E compositions. Many embodiments employ tocotrineol isolated from natural sources such as tocotrienol-enriched fractions obtained from sunflower seed, wheat germ, bran, palm, or other vegetable oils by high performance liquid chromatography or other methods, or tocotrienol-enriched extracts obtained from barley, brewer's grains oats, and other tocotrienol-containing natural products by alcohol extraction, molecular distillation and the like. Useful tocotrienols can be tocotrienol-enriched fractions or extracts, or mixtures of these with vitamin E fractions. As used herein, the term "tocotrienols" includes all of these tocotrienol-rich fractions and extracts obtained from these natural products as well as the pure compounds and mixtures of any of these.

As with other vitamin E preparations, tocotrienol or tocotrienol-enriched preparations include those containing tocotrienol and, in some cases, tocopherol derivatives, particularly stabilized derivatives. These typically include derivatives related to the phenolic hydroxyl functionality, i.e., wherein it is acylated with an organic acid to form an ester. Examples of such stabilized tocotrienols include, but are not limited to, tocotrienol acetate, tocotrienol succinate, and mixtures thereof. However, the derivatives may also include those involving other reactive groups known to those skilled in the art. Where tocotrienol derivatives are employed, they must be functionally equivalent to tocotrienol. Preferred derivatives contain both the chromanol nucleus and three double bonds in the hydrocarbon tail.

While not wishing to be bound to any theory, it is possible that lipoic acid is efficacious in the treatment of scar tissue because it is fat- and watersoluble and readily disperses in cell membranes and other cellular components. It acts as a free radical scavenger and neutralizer, and prevents the cross-linking of cell membranes that is seen in scar formation, particularly keloid scar formation. By the same token, LA modulation of free radicals and other oxidative species affects gene expression, including expression of nuclear factor κ-B (NF-κB), nitric oxide synthetase and other mediators at all stages of proinflammation and inflammation. Lipoic acid's alteration of lipid peroxidation, protein cross-linking, growth factor stimulation, and membrane permability may explain its negative effect on scar tissue formation.

The method of the present invention is particularly useful for reducing or inhibiting scars caused by minor lacerations, surgical wounds, vaccines, burns, and abrasions, as well as stretch marks observed in aging and after weight loss or childbirth and various types of fibroses. Generally, the composition is topically applied to the affected skin areas in a predetermined or as-needed regimen either at intervals by application of a lotion or the like, or continuously using a silicone gel sheet, it generally being the case that gradual improvement is noted with each successive application. Insofar as has been determined based upon clinical studies to date, no adverse side effects are encountered.

The following examples are presented to further illustrate and explain the present invention and should not be taken as limiting in any regard. Unless otherwise indicated, all percentages are by weight.

EXAMPLES

Fifteen patients between the ages of 20 and 57 years who had hypertrophic scars applied a composition containing 5% glycolic acid and 1% α-lipoic acid in a lecithin base to the scars twice daily for a period of three months. The scars were observed and photographed at weeks 4, 8, and 12. Comparison of the assessment photographs with those taken of untreated lesions showed a greater than 50% reduction in lesions in 90% of the patients.

A second study was made on five subjects aged 18 to 30 years having striae distensae. Compositions containing 3% lipoic acid, a 1% tocotrienol-rich palm oil fraction, and 1% ascorbyl palmitate were applied to the striae twice daily for two months. At the end of that period, two of the subjects exhibited an 80% reduction in striae, while the remainder showed a 50% reduction in striae.

The papers and patents cited above are expressly incorporated in their entireties by reference.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

I claim:

1. A method for the treatment of cutaneous scar tissue comprising applying to said tissue a composition containing lipoic acid or a lipoic acid derivative in a dermatologically acceptable carrier.

2. A method according to claim 1 wherein the lipoic acid derivative is selected from the group consisting of dihydrolipoic acid, a lipoic or dihydrolipoic acid ester, a lipoic or dihydrolipoic acid amide, a lipoic or dihydrolipoic acid salt, and mixtures thereof.

3. A method according to claim 1 wherein the composition comprises lipoic acid, dihydrolipoic acid, or mixtures thereof.

4. A method according to claim 1 wherein the composition comprises from about 0.1% to about 7% lipoic acid or lipoic acid derivative.

5. A method according to claim 4 comprising from about 1% to about 5% by weight of lipoic acid or a lipoic acid derivative.

6. A method according to claim 5 comprising from about 2% to about 3% by weight of lipoic acid or a lipoic acid derivative.

7. A method according to claim 3 wherein the composition comprises lipoic acid.

8. A method according to claim 1 wherein the composition comprises lipoamide.

9. A method according to claim 1 wherein the scar tissue is hypertrophic scar tissue.

10. A method according to claim 1 wherein the scar tissue is striae distensae.

11. A method according to claim 1 wherein the composition is applied at intervals to the scar tissue.

12. A method according to claim 1 wherein the composition is applied continuously using a silicone gel sheet.

13. A method for the treatment of cutaneous scar tissue comprising applying to said tissue a composition containing an active ingredient selected from the group consisting of lipoic acid, dihydrolipoic acid, lipoamide, and mixtures thereof, in amounts effective to reduce the scar tissue.

14. A method according to claim 13 wherein the composition contains from about 0.1% to 7% active ingredient.

15. A method according to claim 14 wherein the composition contains from about 1% to about 5% active ingredient.

16. A method according to claim 15 wherein the composition contains from about 2% to about 3% active ingredient.

17. A method according to claim 13 wherein the active ingredient is lipoic acid.

18. A method according to claim 13 wherein the active ingredient is dihydrolipoic acid.

19. A method according to claim 13 wherein the active ingredient is lipoamide.

20. A method according to claim 13 wherein the composition is applied at intervals to the scar tissue.

21. A method according to claim 13 wherein the composition is applied continuously using a silicone gel sheet.

22. A method according to claim 13 wherein the scar tissue is hypertrophic scar tissue.

23. A method according to claim 13 wherein the scar tissue is striae distensae.

24. A method for the treatment of cutaneous scars to diminish the scar tissue comprising applying to said scars a composition containing from about 0.1% to about 7% of an active ingredient selected from the group consisting of lipoic acid, dihydrolipoic acid, lipoamide, and mixtures thereof, in a dermatologically acceptable carrier.

25. A method according to claim 24 wherein the scars are hypertrophic scars.

26. A method according to claim 24 wherein the scars are striae distensae.

27. A method according to claim 24 wherein the composition comprises from about 1% to about 5% active ingredient.

28. A method according to claim 27 wherein the composition comprises from about 2% to about 3% active ingredient.

29. A method according to claim 24 wherein the active ingredient is lipoic acid.

30. A method according to claim 24 wherein the active ingredient is dihydrolipoic acid.

31. A method according to claim 24 wherein the active ingredient is lipoamide.

32. A method according to claim 24 wherein the composition is applied at intervals to the scar tissue.

33. A method according to claim 24 wherein the composition is applied continuously using a silicone gel sheet.

34. A method for diminishing cutaneous scar tissue caused by minor lacerations, surgical wounds, vaccines, burns, fibroses, and stretch marks comprising applying to the tissue a composition containing from about 0.1% to about 7% of an active ingredient selected from the group consisting of lipoic acid, dihydrolipoic acid, lipoamide, and mixtures thereof, in a dermatologically acceptable carrier.

* * * * *